United States Patent [19]

Hutchins

[11] 4,138,639
[45] Feb. 6, 1979

[54] FLUID CONDUCTIVITY MEASUREMENT

[76] Inventor: Thomas B. Hutchins, 310 NW. Brynwood La., Portland, Oreg. 97229

[21] Appl. No.: 815,585

[22] Filed: Jul. 14, 1977

[51] Int. Cl.² .................................................. G01N 27/42
[52] U.S. Cl. ................................. 324/30 A; 324/30 R
[58] Field of Search ....................... 324/29, 30 R, 30 A

[56] References Cited

U.S. PATENT DOCUMENTS

| | | | |
|---|---|---|---|
| 3,054,946 | 9/1962 | Esterson | 324/30 A |
| 3,404,336 | 10/1968 | Rosenthal | 324/30 A |

*Primary Examiner*—M. Tokar
*Attorney, Agent, or Firm*—Kolisch, Hartwell, Dickinson & Stuart

[57] ABSTRACT

Fluid conductivity measuring apparatus employing fluid-coupled primary and secondary transformer windings where the primary transformer winding is energized by an oscillator. Accuracy in the apparatus is enhanced through the use therein of a feedback winding in the primary section of the transformer which couples with an output-level-control input in the oscillator to inhibit any tendency of the signal output level of the oscillator to change.

2 Claims, 1 Drawing Figure

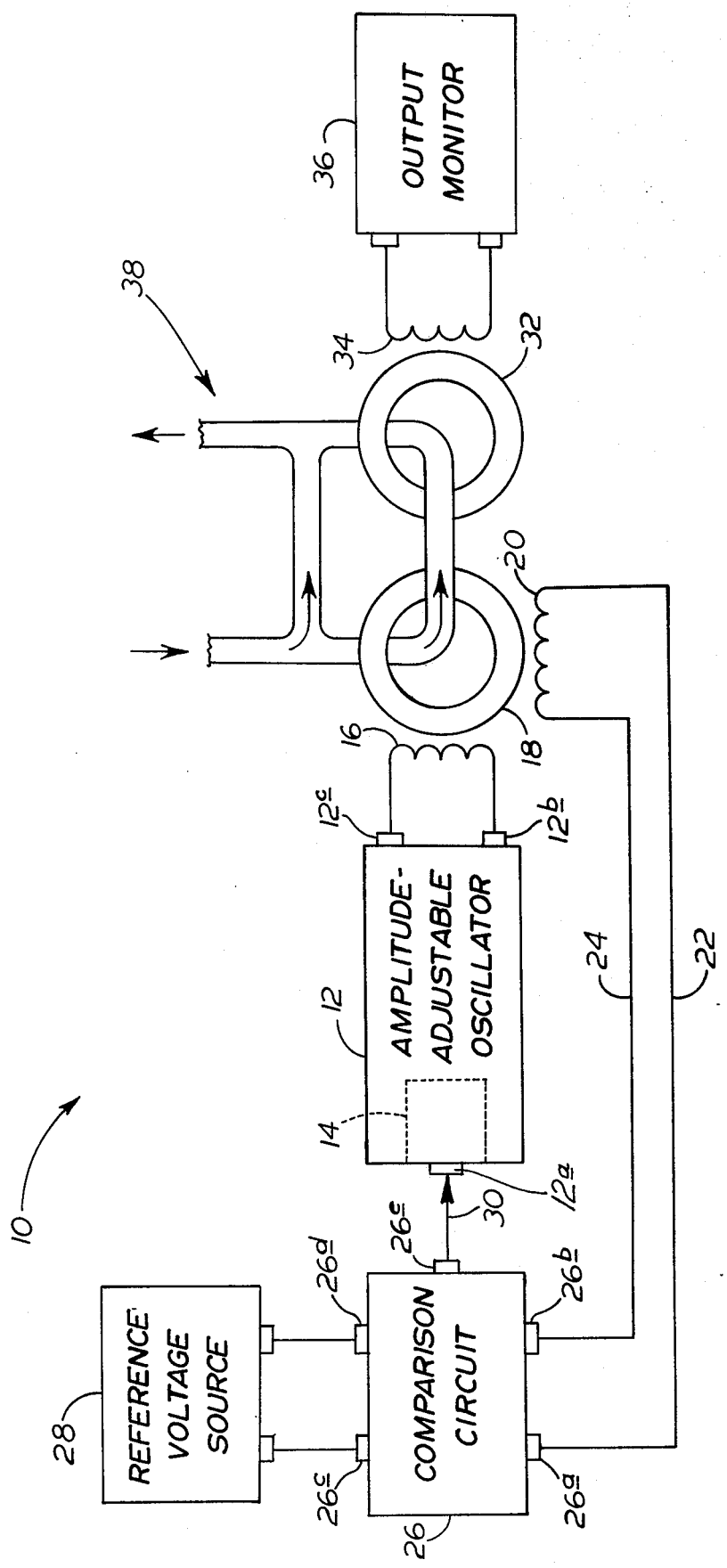

FLUID CONDUCTIVITY MEASUREMENT

BACKGROUND AND SUMMARY OF THE INVENTION

This invention pertains to the monitoring of the electrical conductivity in a fluid. For the purpose of explanation herein, a preferred embodiment of the invention is described in conjunction with the monitoring of the electrical conductivity in a dialysate fluid which is used in conventional kidney-patient dialysis.

There are many applications where it is desirable and important to monitor the conductivity of a fluid. Further, there are many such applications wherein it is desirable to be able to accomplish such monitoring without directly contacting, and perhaps interfering with the chemistry of, a fluid.

One application wherein the present invention has been found to have a particular utility is in the monitoring of the dialysate used in kidney-patient dialysis. It is typical during dialysis to mix, on a continuous basis, a dialysate concentrate with water to produce a dialysate fluid having a prescribed concentration. It is important that such concentration be held within certain limits, and thus, monitoring of the condition of the dialysate is also important.

Methods and apparatus have been proposed in the past for such monitoring through following the electrical conditions in the prepared dialysate. However, these various methods either involve direct contact with the dialysate, or have had inherent instability problems which have made it difficult accurately to follow the important minute changes which may be taking place in the mixture.

The present invention proposes a unique apparatus for accomplishing such monitoring while avoiding problems that attend prior art attempts in the same direction.

Thus, a general object of the present invention is to provide electrical apparatus for measuring the conductivity of a fluid, such as a dialysate, which apparatus accomplishes this purpose without requiring contacting of such a fluid, and with means provided for stabilizing the apparatus so as to furnish maximum accuracy.

A preferred embodiment of the invention features measuring apparatus employing fluid-coupled primary and secondary transformer windings, with the primary winding energized by an oscillator. Output signals are derived from the secondary winding. Enhancing the accuracy of the apparatus, and more specifically, minimizing the likelihood of an error being introduced as the result of a change in the signal output level of the oscillator, is a feedback winding which is used in the primary section of the transformer. This feedback winding couples with an output-level control input in the oscillator in such a manner that the output level of the oscillator is stabilized.

Various other objects and advantages which are attained by the invention will become more fully apparent as the description which now follows is read in conjunction with the accompanying drawing which shows, schematically, the apparatus of the invention set up to monitor the conductivity of a dialysate liquid.

DETAILED DESCRIPTION OF THE INVENTION

Turning now to the single drawing FIGURE, indicated generally at 10 is apparatus, as proposed by the present invention, for measuring the conductivity of a fluid. In the particular application depicted in FIG. 1, apparatus 10 is set up to monitor the conductivity of a flowing dialysate used during the process of kidney-patient dialysis.

Included in apparatus 10 is an electronic amplitude-adjustable, or output-level-controllable, oscillatoe, which operates herein at a frequency of around four kilohertz. Included within oscillator 12, and represented by dashed block 14 therein, is a sub-circuit which responds to a DC control voltage, at the oscillator's output-level-control input 12a to effect changes in the oscillator's amplitude level. Oscillator 12 and subcircuit 14 therein, may be of entirely conventional construction, and hence are not shown herein in any detail. The output terminals of oscillator 12, shown at 12b, 12c are connected to a winding 16 which is wrapped on a high-magnetic-permeability ferrite torroidal core 18. Through winding 16, an output signal generated by oscillator 12 is coupled into core 18. Winding 16 is referred to herein as a primary transformer winding.

Indicated at 20 is a feedback winding, or means, which is also wound on core 18. The opposite ends of this winding are connected through conductors 22, 24 to terminals 26a, 26b in a comparison circuit 26. Circuit 26 also includes terminals 26c, 26d which are connected to the output terminals of any suitable regulated DC reference voltage source 28. Comparison circuit 26, like oscillator 12, is of conventional design and construction. AC signals fed to the comparison circuit from winding 20 are converted into a related-level DC voltage, the level of which is compared with that of reference voltage source 28. Any difference between these two voltages produces a related DC control voltage on output terminal 26e in the comparison circuit. The polarity of this control voltage is an indication whether DC voltage derived from the voltage produced in winding 20 is higher or lower than that presented by source 28. In apparatus 10, with the voltage derived from winding 20 being larger than that derived from source 28, a negative-going control voltage is produced. The reverse situation is true with the voltage derived from the feedback winding being lower than that derived from source 28.

Control voltage produced at output 26e is coupled through a conductor 30 to output-level-control input 12a of oscillator 12. An increase in a positive direction in the control voltage causes the oscillator output level to rise in direct proportion. The reverse is true with a decrease in control voltage. Suitable means, which are also of conventional design, are incorporated in the oscillator and in the comparison circuit to stabilize these circuits against temperature changes.

With the arrangement just described, any tendency of the output level of the oscillator to rise, causes an increase in voltage induced in feedback winding 20, which in turn ultimately effects a related downward adjustment of the output level of the oscillator. The reverse situation takes place with any tendency of the output level of the oscillator to decrease. As a consequence, and with suitable calibration well within the skill of those skilled in the art, oscillator 12 is feedback-stabilized with respect to its output amplitude, so that the signal level which it couples into core 18 is substantially constant.

Further describing apparatus 10, indicated at 32 is another core which, herein, is a substantial duplicate of core 18. Wound on core 32 is a winding 34, referred to as a secondary winding, the opposite ends of which feed the input terminals of an output monitor circuit, or signal output means, 36. The output monitor circuit may be of any suitable conventional design which ultimately converts the AC signal furnished from winding 34 into a related DC signal whose level may be followed in any suitable manner. Preferably, and in order substantially to eliminate any flux-induced permeability changes in cores 18, 20 which could affect the level of the signal developed in winding 34, the input terminals of circuit 36 feed into a zero-input-impedance amplifier. Such is the case in circuit 36.

It is important in the construction of the apparatus so far described that cores 18, 32 be rigidly mounted with respect to each other so that their relative disposition remains constant. This, of course, may be accomplished in any suitable manner.

Dialysate whose conductivity is to be monitored by apparatus 10 is conducted toward and away from the apparatus through a plumbing, or fluid conduit, system shown generally at 38. The direction of flow in system 38 is indicated by the arrows in the figure. This system is suitably connected in the dialysate flow-circuit of a dialysis machine (omitted from the figure). As was true in the case of the relative positioning of cores 18, 32, it is important that that portion of system 38 which links cores 18, 32 be made of a dimensionally stable rigid construction, and be anchored in a fixed position relative to the cores. There are various suitable rigid electrically insulative materials which may be used for this purpose. As can be seen in the figure, plumbing system 38 terminates in what appears to be a generally rectangular loop that couples the cores. The exact shape of the plumbing system is a matter of choice.

When apparatus 10 is placed in use, a signal is fed by oscillator 12 through winding 16 into core 18. This signal is picked up by feedback winding 20, and is used, through the means previously discussed, to stabilize the output level of the oscillator. With dialysate present in system 38, and more particularly flowing in the system, cores 18, 32 are coupled by that rectangular-loop portion of the plumbing system which links the cores. The amount of energy thus coupled from core 18 to core 32 is in direct proportion to the electrical conductivity of the dialysate. Hence, the output signal developed in winding 34, and indicated by monitoring circuit 36, is also in direct proportion to such conductivity. Because of the level-stabilization accomplished for oscillator 12, and because of conventional temperature compensation used in the oscillator and in the comparison circuit, and further, because of the inputing of a signal from winding 34 to a zero-input-impedance amplifier in circuit 36, an extremely stable and accurate liquid-conductivity measuring system is provided. In this system, any change detected in the signal developed in winding 34 is substantially directly and completely relatable to changes in the conductivity level of the dialysate flowing in the plumbing system.

While a preferred embodiment of the invention has been described herein, it is appreciated that variations and modifications may be made without departing from the spirit of the invention.

It is claimed and desired to secure by Letters Patent:

1. Electrical apparatus with feedback stabilization for measuring the conductivity of a fluid comprising
    spaced primary and secondary transformer winding means,
    fluid conduit means, for containing a fluid whose conductivity is to be measured, electrically coupling said winding means,
    output-level-controllable oscillator means connected to energize said primary winding means and including an output-level-control input,
    feedback means operatively coupling said primary winding means and said input, operable, with said oscillator means oscillating, and in cooperation with said input and said primary means, to inhibit any tendency of the output level of the oscillator means to change, and
    signal output means operatively connected to said secondary winding means, constructed, with said apparatus functioning, to produce an output signal having an electrical characteristic which is directly relatable to the conductivity of any fluid contained in said fluid conduit means.

2. The apparatus of claim 1, wherein said signal output means includes a zero-input-impedancy amplifier.

* * * * *